US007655817B2

(12) United States Patent
Takemoto et al.

(10) Patent No.: US 7,655,817 B2
(45) Date of Patent: Feb. 2, 2010

(54) PRODUCTION METHODS OF OPTICALLY ACTIVE HYDRAZINE COMPOUND AND OPTICALLY ACTIVE AMINE COMPOUND

(75) Inventors: Yoshiji Takemoto, Shiga (JP); Kazuo Murakami, Nara (JP)

(73) Assignees: Kyoto University, Kyoto (JP); Sumitomo Chemical Company, Limited, Tokyo (JP)

( * ) Notice: Subject to any disclaimer, the term of this patent is extended or adjusted under 35 U.S.C. 154(b) by 609 days.

(21) Appl. No.: 11/341,852

(22) Filed: Jan. 30, 2006

(65) Prior Publication Data
US 2006/0194986 A1 Aug. 31, 2006

(30) Foreign Application Priority Data
Feb. 28, 2005 (JP) ............................. 2005-054799

(51) Int. Cl.
C07C 241/02 (2006.01)
(52) U.S. Cl. ............................. 564/310; 564/17; 564/32
(58) Field of Classification Search ........................ None
See application file for complete search history.

(56) References Cited
FOREIGN PATENT DOCUMENTS
WO WO 2005/000803 A2 1/2005

OTHER PUBLICATIONS

Bøgevig et al., "Direct Organo-Catalytic Asymmetric α-Amination of Aldehydes—A Simple Approach to Optically Active α-Amino Aldehydes, α-Amino Alcohols, and α-Amino Acids," Angew. Chem. Int. Ed., 2002, vol. 41, No. 10, pp. 1790-1793.
Chowdari et al., "Total Synthesis of LFA-1 Antagonist BIRT-377 via Organocatalytic Asymmetric Construction of a Quaternary Stereocenter," Organic Letters, 2005, vol. 7, No. 5, pp. 867-870.
Duthaler, Rudolf O., "Proline-Catalyzed Asymmetric α-Amination of Aldehydes and Ketones—An Astonishingly Simple Access to Optically Active α-Hydrazino Carbonyl Compounds," Angew. Chem. Int. Ed., 2003, vol. 42, pp. 975-978.
U.S. Appl. No. 10/562,579, filed Dec. 27, 2005, Yoshiji Takemoto.
Ishitani et al., "Catalytic, Enantioselective Synthesis of α-Aminonitriles with a Novel Zirconium Catalyst," Angew. Chem. Int. Ed., 1998, vol. 37, No. 22, pp. 3186-3188.
Ishitani et al., "Catalytic Asymmetric Strecker Synthesis. Preparation of Enantiomerically Pure α-Amino Acid Derivatives from Aldimines and Tributyltin Cyanide or Achiral Aldehydes, Amines, and Hydrogen Cyanide Using a Chiral Zirconium Catalyst," J. Am. Chem. Soc., 2000, vol. 122, pp. 762-766.
Ishitani et al., "Catalytic Enantioselective Mannich-Type Reactions Using a Novel Chiral Zirconium Catalyst," J. Am. Chem. Soc., 1997, vol. 119, pp. 7153-7154.
Ishitani et al., "Enantioselective Mannich-Type Reactions Using a Novel Chiral Zirconium Catalyst for the Synthesis of Optically Active β-Amino Acid Derivatives," J. Am. Chem. Soc., 2000, vol. 122, pp. 8180-8186.

Kobayashi et al., "The Catalyst Asymmetric Mannich-Type Reactions in Aqueous Media," J. Am. Chem. Soc., 2002, vol. 124, pp. 5640-5641.

(Continued)

Primary Examiner—Zinna N Davis
(74) Attorney, Agent, or Firm—Foley & Lardner LLP

(57) ABSTRACT

The present invention relates to a production method of optically active hydrazine compound (IV), which includes reacting azo compound (II) with compound (III) in the presence of optically active compound (I). The present invention also relates to a production method of optically active amine compound (V), which includes producing optically active hydrazine compound (IV) by the above-mentioned method, reacting the optically active hydrazine compound (IV) with a base or an acid to eliminate a protecting group represented by PG, and then subjecting the resulting compound to catalytic reduction or reacting the resulting compound with a zinc powder to reduce a nitrogen-nitrogen bond.

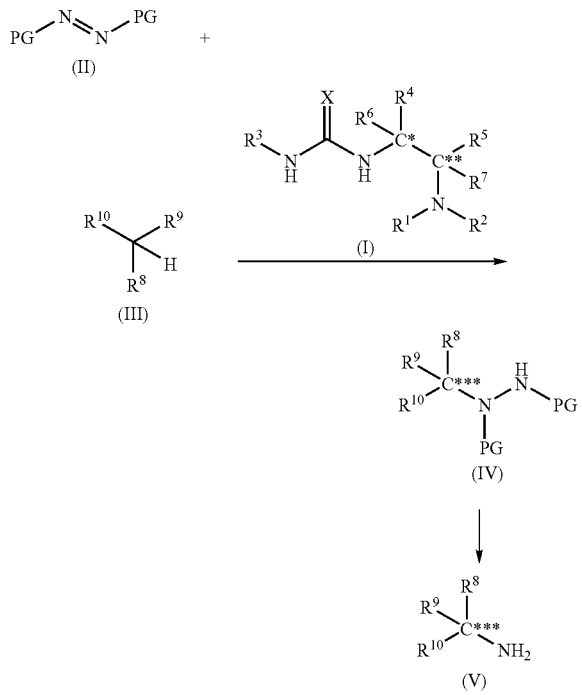

wherein X is S or O; C*, C and C* are asymmetric carbons, $R^1$ and $R^2$ are lower alkyl groups etc., $R^4$ and $R^5$ may in combination form cyclohexane etc., $R^3$ is aryl group optionally having substituent(s) etc., $R^6$ and $R^7$ are hydrogen atoms etc., $R^8$ is aryl group optionally having substituent(s) etc., $R^9$ and $R^{10}$ are electron withdrawing groups, and PG is a protecting group.

11 Claims, No Drawings

OTHER PUBLICATIONS

Kumaragurubaran et al., "Direct $_L$-Proline-Catalyzed Asymmetric α-Amination of Ketones," J. Am. Chem. Soc., 2002, vol. 124, pp. 6254-6255.

List, Benjamin, "Direct Catalytic Asymmetric α-Amination of Aldehydes," J. Am. Chem. Soc. 2002, vol. 124, pp. 5656-5657.

Liu et al., "Highly Enantioselective Amination of α-Substituted α-Cyanoacetates with Chiral Catalysts Accessible from Both Quinine and Quinidine," Organic Letters, 2005, vol. 7, No. 2, pp. 167-169.

Marigo et al., "Catalytic, Highly Enantioselective, Direct Amination of β-Ketoesters," Angew. Chem. Ind. Ed., 2003, vol. 42, No. 12, pp. 1367-1369.

Pihko et al., "Enantioselective Organocatalytic Diels Aminations: α-Aminations of Cyclic β-Keto Esters and β-Keto Lactones with Cinchonidine and Cinchonine," Synlett, 2004, No. 12, pp. 2115-2118.

Saaby et al., "Asymmetric Construction of Quaternary Stereocenters by Direct Organocatalytic Amination of α-Substituted α-Cyanoacetates and β-Dicarbonyl Compounds," J. Am. Chem. Soc., 2004, vol. 126, pp. 8120-8121.

Sigman et al., "Enantioselective Addition of Hydrogen Cyanide to Imines Catalyzed by a Chiral (Salen)AI(III) Complex," J. Am. Chem. Soc., 1998, vol. 120, pp. 5315-5316.

Sigman et al., "A General Catalyst for the Asymmetric Strecker Reaction," Angew. Chem. Int. Ed., 2000, vol. 39, No. 7, pp. 1279-1281.

Suri et al., "Organocatalytic Enantioselective Synthesis of Metabotropic Glutamate Receptor Ligands," Organic Letters, 2005, vol. 7, No. 18, pp. 3885-3888.

PRODUCTION METHODS OF OPTICALLY ACTIVE HYDRAZINE COMPOUND AND OPTICALLY ACTIVE AMINE COMPOUND

TECHNICAL FIELD OF THE INVENTION

The present invention relates to a production method of an optically active hydrazine compound and a production method of an optically active amine compound, which use an optically active thiourea or urea compound as an asymmetric catalyst.

BACKGROUND OF THE INVENTION

There exist a number of biologically active compounds in nature, which are expected to be applicable to pharmaceutical products, such as lactacystin, myriocin, kaitocephalin, oxazolomycin and the like. All of these have an α-amino acid structure having an optically active quaternary carbon, and are considered to be deeply involved with physiological activity.

Therefore, construction of an asymmetric tetrasubstituted carbon center containing a nitrogen atom has been an important object of organic synthetic chemistry, and various synthesis methods have been reported.

The reported methods include a synthesis method of an optically active α-amino acid derivative based on the construction of an enantioselective carbon-carbon bond, which employs Strecker reaction or Mannich reaction (see references 1-7 below), and a synthesis method based on the construction of an enantioselective carbon-nitrogen bond, which employs proline, cinchonidine, 2,2'-isopropylidenebis(4-phenyl-2-oxazoline) (Ph-BOX) or β-isocupreidine as a catalyst (see references 8-14 below).

1. Journal of the American Chemical Society, (USA), 1998, Vol. 120, p. 5315
2. Angewandte Chemie International Edition, 2000, Vol. 39, p. 1279
3. Angewandte Chemie International Edition, 1998, Vol. 37, p. 3186
4. Journal of the American Chemical Society, (USA), 2000, Vol. 122, p. 762
5. Journal of the American Chemical Society, (USA), 1997, Vol. 119, p. 7153
6. Journal of the American Chemical Society, (USA), 2002, Vol. 124, p. 5640
7. Journal of the American Chemical Society, (USA), 2000, Vol. 122, p. 8180
8. Angewandte Chemie International Edition, 2002, Vol. 41, p. 1790-1793
9. Journal of the American Chemical Society, (USA), 2002, Vol. 124, p. 5656-5657
10. Journal of the American Chemical Society, (USA), 2002, Vol. 124, p. 6254-6255
11. Angewandte Chemie International Edition, 2003, Vol. 42, p. 975-978
12. Synlett, (USA), 2004, Vol. 12, p. 2115-2118
13. Angewandte Chemie International Edition, 2003, Vol. 42, p. 1367-1369
14. Journal of the American Chemical Society, (USA), 2004, Vol. 126, p. 8120-8121

SUMMARY OF THE INVENTION

The problem to be solved by the present invention is provision of an advantageous production method of an optically active compound having a carbon-nitrogen bond, which is useful as an intermediates for synthesizing amines, amino acids, pharmaceutical agents, agricultural chemicals, food additives and the like, and which is based on the development of an enantioselective carbon-nitrogen bond formation reaction using an environmentally less burdening non-metallic asymmetric catalyst.

To solve the above-mentioned problems, the present inventors took note of a compound wherein both of an acidic moiety that activates an azo compound and a basic moiety that activates a carbon atom having active hydrogen are bonded to optically active scaffolds, as a non-metallic asymmetric catalyst, and conducted intensive studies. As a result, they have found that the carbon-nitrogen bond formation reaction by enantioselective addition of carbanion to an azo compound proceeds in a high yield and highly stereoselectively by the use of an optically active thiourea or urea compound as a non-metallic asymmetric catalyst, which resulted in the completion of the present invention.

Accordingly, the present invention provides the following.

[1] A production method of a compound represented by the formula (IV):

wherein $R^8$ is a hydrogen atom, a lower alkyl group optionally having substituent(s), an aralkyl group optionally having substituent(s), an aryl group optionally having substituent(s) or a heteroaryl group optionally having substituent(s);

$R^9$ and $R^{10}$ are each independently an electron withdrawing group, or $R^8$ and $R^9$ optionally form, together with the adjacent carbon atom, a ring containing an electron withdrawing group and optionally having substituent(s) (said ring is optionally condensed with an aromatic hydrocarbon), provided that $R^9$ and $R^{10}$ are not the same group;

C*** is an asymmetric carbon; and

PG is a protecting group

[hereinafter to be also referred to as optically active hydrazine compound (IV)] or a salt thereof, which comprises reacting a compound represented by the formula (II):

wherein PG is as defined above [hereinafter to be also referred to as azo compound (II)], with a compound represented by the formula (III):

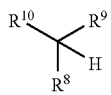
(III)

wherein $R^8$, $R^9$ and $R^{10}$ are as defined above [hereinafter to be also referred to as compound (III)], in the presence of a compound represented by the formula (I):

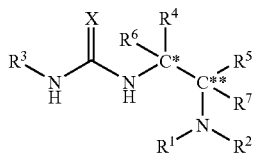
(I)

wherein

X is S or O;

C* and C** are each independently an asymmetric carbon;

$R^1$ and $R^2$ are
the same or different and each is a lower alkyl group optionally having substituent(s), an aralkyl group optionally having substituent(s) or an aryl group optionally having substituent(s), or $R^1$ and $R^2$ optionally form, together with the nitrogen atom they are bonded to, an aliphatic heterocycle optionally having substituent(s) (the aliphatic heterocycle is optionally condensed with an aromatic hydrocarbon);

$R^3$ is
a lower alkyl group optionally having substituent(s), an aralkyl group optionally having substituent(s), an aryl group optionally having substituent(s) or a heteroaryl group optionally having substituent(s);

$R^4$ and $R^5$ are
the same or different and each is a lower alkyl group optionally having substituent(s), an aralkyl group optionally having substituent(s) or an aryl group optionally having substituent(s), or $R^4$ and $R^5$ optionally form, together with the asymmetric carbons they are respectively bonded to, a homocyclic ring optionally having substituent(s) or a heterocycle optionally having substituent(s) (the homocyclic ring and the heterocycle are each optionally condensed with an aromatic hydrocarbon); and $R^6$ and $R^7$ are
the same or different and each is a hydrogen atom or a lower alkyl group optionally having substituent(s),

[hereinafter to be also referred to as optically active compound (I)], or a salt thereof.

[2] The method of the above-mentioned [1], wherein X is S.

[3] The method of the above-mentioned [1] or [2], wherein $R^4$ and $R^5$ form, together with the asymmetric carbons they are respectively bonded to, cyclopropane, cyclobutane, cyclopentane or cyclohexane.

[4] The method of the above-mentioned [3], wherein $R^4$ and $R^5$ form cyclohexane together with the asymmetric carbons they are respectively bonded to, and $R^6$ and $R^7$ are each a hydrogen atom.

[5] The method of the above-mentioned [4], wherein the absolute configurations of C* and C** are both S-configurations or both R-configurations.

[6] The method of any of the above-mentioned [1] to [5], wherein the protecting group is —$CO_2R^{11}$ or —$CONR^{12}R^{13}$ wherein $R^{11}$, $R^{12}$ and $R^{13}$ are each independently a lower alkyl group optionally having substituent(s), an aralkyl group optionally having substituent(s), an aryl group optionally having substituent(s) or a heteroaryl group optionally having substituent(s), or $R^{12}$ and $R^{13}$ optionally form, together with the nitrogen atom they are bonded to, an aliphatic heterocycle optionally having substituent(s) (the aliphatic heterocycle is optionally condensed with an aromatic hydrocarbon).

[7] The method of any of the above-mentioned [1] to [6], wherein the electron withdrawing group is a cyano group, a nitro group, —P(=O)$R^{14}R^{15}$, —$SO_2R^{16}$, —$CO_2R^{17}$, —$CONR^{18}R^{19}$ or —$COR^{20}$ wherein $R^{14}$, $R^{15}$, $R^{16}$, $R^{17}$, $R^{18}$, $R^{19}$ and $R^{20}$ are each independently a hydrogen atom, a lower alkyl group optionally having substituent(s), an aralkyl group optionally having substituent(s), an aryl group optionally having substituent(s) or a heteroaryl group optionally having substituent(s), or $R^{18}$ and $R^{19}$ optionally form, together with the nitrogen atom they are bonded to, an aliphatic heterocycle optionally having substituent(s) (the aliphatic heterocycle is optionally condensed with an aromatic hydrocarbon).

[8] The method of any of the above-mentioned [1] to [6], wherein the ring containing an electron withdrawing group, which is optionally formed by $R^8$ and $R^9$ is cyclopentanone, cyclohexanone, 1-indanone or 1,2,3,4-tetrahydro-1-oxonaphthalene.

[9] The method of any of the above-mentioned [1] to [8], wherein the reaction is performed in at least one solvent selected from toluene, methylene chloride, diethyl ether and hexane.

[10] A production method of a compound represented by the formula (V):

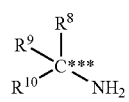
(V)

wherein each symbol is as defined above [hereinafter to be also referred to as optically active amine compound (V)] or a salt thereof, which comprises reacting azo compound (II) with compound (III) in the presence of optically active compound (I) or a salt thereof to give optically active hydrazine compound (IV) or a salt thereof, reacting the optically active hydrazine compound (IV) or a salt thereof with a base or an acid to eliminate the protecting group represented by PG, and then subjecting the resulting compound to catalytic reduction or reacting the resulting compound with a zinc powder to reduce a nitrogen-nitrogen bond.

[11] The method of the above-mentioned [10], wherein X is S.

According to the present invention, optically active hydrazine compound (IV) can be produced in a high yield and highly stereoselectively by the use of a non-metallic optically active compound (I) as an asymmetric catalyst and by the addition of compound (III) to azo compound (II). The obtained optically active hydrazine compound (IV) can be easily led to optically active amine compound (V) by cleaving the nitrogen-nitrogen bond.

Since the optically active compound (I) of the present invention is non-metallic and does not require treatments of metal waste liquid and the like, it is an environmentally-friendly catalyst. Moreover, since it is non-metallic, the compound can be recovered and reused easily.

BEST MODE FOR EMBODYING THE INVENTION

The present invention is described in detail in the following.

1. Definition of Symbols and Terms

The alkyl used in the present invention is linear when it is free of a prefix (e.g., iso, neo, sec-, tert- and the like). For example, a simple propyl means linear propyl.

The "lower alkyl group" of the "lower alkyl group optionally having substituent(s)" for $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{17}$, $R^{18}$, $R^{19}$ or $R^{20}$ is a straight chain or branched chain alkyl group having 1 to 12 carbon atoms, and, for example, methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl and the like can be mentioned. Preferred is an alkyl group having 1 to 8 carbon atoms, and more preferred are methyl, ethyl, propyl and isopropyl.

The lower alkyl group optionally has substituent(s) at substitutable position(s), and as such substituent(s), a lower alkoxy group, a mono-lower alkylamino group, a di-lower alkylamino group, a halogen atom, an aralkyloxy group (e.g., benzyloxy, α- or β-naphthylmethoxy etc.), an allyloxy group, a propargyloxy group, a nitro group, a cyano group, —COOR$^{21}$ wherein $R^{21}$ is a lower alkyl group as defined above, and the like can be mentioned. The number of substituents is not particularly limited, but is preferably 1 to 3. When it is 2 or more, the substituents may be the same or different.

The "lower alkoxy group" is an alkoxy group wherein the alkyl moiety is the "lower alkyl group" defined above, and, for example, methoxy, ethoxy, propoxy, isopropoxy, butoxy, isobutoxy, sec-butoxy, tert-butoxy, pentoxy, isopentoxy, neopentoxy, hexyloxy, heptyloxy, octyloxy, nonyloxy, decyloxy, undecyloxy, dodecyloxy and the like can be mentioned. Preferred are methoxy and ethoxy.

The "mono-lower alkylamino group" is a mono-alkylamino group wherein the alkyl moiety is the "lower alkyl group" defined above, and, for example, N-methylamino, N-ethylamino, N-propylamino, N-isopropylamino, N-butylamino, N-isobutylamino, N-sec-butylamino, N-tert-butylamino, N-pentylamino, N-isopentylamino, N-neopentylamino, N-hexylamino, N-heptylamino, N-octylamino, N-nonylamino, N-decylamino, N-undecylamino, N-dodecylamino and the like can be mentioned.

The "di-lower alkylamino group" is a di-alkylamino group wherein the alkyl moieties are the same or different and each is the "lower alkyl group" defined above, and, for example, N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dipentylamino, N,N-diisopentylamino, N,N-dineopentylamino, N,N-dihexylamino, N,N-diheptylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-tert-butylamino, N-methyl-N-pentylamino, N-methyl-N-isopentylamino, N-methyl-N-neopentylamino, N-methyl-N-hexylamino, N-methyl-N-heptylamino, N-methyl-N-octylamino, N-methyl-N-nonylamino, N-methyl-N-decylamino, N-methyl-N-undecylamino, N-methyl-N-dodecylamino and the like can be mentioned.

The "halogen atom" is fluorine atom, chlorine atom, bromine atom or iodine atom, and preferred are chlorine atom and bromine atom.

The "aryl group" of the "aryl group optionally having substituent(s)" for $R^1$, $R^2$, $R^3$, $R^4$, $R^5$, $R^8$, $R^{11}$, $R^{12}$, $R^{13}$, $R^{14}$, $R^{15}$, $R^{16}$, $R^{17}$, $R^{18}$, $R^{19}$ or $R^{20}$ is an aryl group having 6 to 20 carbon atoms, and, for example, phenyl, 1- or 2-naphthyl, biphenyl, binaphthyl and the like can be mentioned.

The aryl group optionally has substituent(s) at substitutable position(s), and as such substituent(s), a lower alkyl group (exemplified by those defined above), a lower alkoxy group (exemplified by those defined above), a mono-lower alkylamino group (exemplified by those defined above), a di-lower alkylamino group (exemplified by those defined above), a halogen atom (exemplified by those defined above), a haloalkyl group (lower alkyl group substituted by one or more halogen atoms, such as trifluoromethyl etc.), an aralkyloxy group (exemplified by those defined above), an allyloxy group, a propargyloxy group, a nitro group, a cyano group, —COOR$^{21}$ wherein $R^{21}$ is as defined above, and the like can be mentioned. The number of substituents is not particularly limited, but is preferably 1 to 3. When it is 2 or more, the substituents may be the same or different.

The "substituent" of the "aryl group optionally having substituent(s)" for $R^3$ is preferably a lower alkyl group, a haloalkyl group, a nitro group, a cyano group, —COOR$^{21}$ wherein $R^{21}$ is as defined above, and the like, more preferably a haloalkyl group and the like.

The "aralkyl group" of the "aralkyl group optionally having substituent(s)" for $R^1$, $R^2$, $R^3$, $R^4$, $R^5$, $R^8$, $R^{11}$, $R^{12}$, $R^{13}$, $R^{14}$, $R^{15}$, $R^{16}$, $R^{17}$, $R^{18}$, $R^{19}$ or $R^{20}$ is an aralkyl group wherein the "lower alkyl group" defined above is substituted by the "aryl group" defined above at optional position(s), and, for example, benzyl, 1- or 2-phenethyl, 1-, 2- or 3-phenylpropyl, 1- or 2-naphthylmethyl, benzhydryl, trityl and the like can be mentioned.

The aralkyl group optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "heteroaryl group" of the "heteroaryl group optionally having substituent(s)" for $R^3$, $R^8$, $R^{11}$, $R^{12}$, $R^{13}$, $R^{15}$, $R^{16}$, $R^{17}$, $R^{18}$, $R^{19}$ or $R^{20}$, for example, a 5- to 10-membered aromatic heterocyclic group containing, besides carbon atoms, 1 to 4 (preferably 1 to 3) hetero atoms selected from an oxygen atom, a sulfur atom and a nitrogen atom, and a fused heterocyclic group thereof and the like can be mentioned. For example, 2- or 3-thienyl, 2- or 3-furyl, 1-, 2- or 3-pyrrolyl, 1-, 2-, 4- or 5-imidazolyl, 2-, 4- or 5-oxazolyl, 2-, 4- or 5-thiazolyl, 1-, 3-, 4- or 5-pyrazolyl, 3-, 4- or 5-isoxazolyl, 3-, 4- or 5-isothiazolyl, 1,2,4-triazol-1, 3, 4 or 5-yl, 1,2,3-triazol-1, 2 or 4-yl, 1H-tetrazol-1 or 5-yl, 2H-tetrazol-2 or 5-yl, 2-, 3- or 4-pyridyl, 2-, 4- or 5-pyrimidinyl, 1-, 2-, 3-, 4-, 5-, 6- or 7-indolyl, 2-, 3-, 4-, 5-, 6- or 7-benzofuryl, 2-, 3-, 4-, 5-, 6- or 7-benzothienyl, 1-, 2-, 4-, 5-, 6- or 7-benzimidazolyl, 2-, 3-, 4-, 5-, 6-, 7- or 8-quinolyl, 1-, 3-, 4-, 5-, 6-, 7- or 8-isoquinolyl and the like can be mentioned.

The heteroaryl group optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

The "substituent" of the "heteroaryl group optionally having substituent(s)" for $R^3$ is preferably a lower alkyl group, a haloalkyl group, a nitro group, a cyano group, —COOR$^{21}$ wherein $R^{21}$ is as defined above, and the like.

Examples of the "aliphatic heterocycle" of the "aliphatic heterocycle optionally having substituent(s)", which $R^1$ and $R^2$, $R^{12}$ and $R^{13}$, or $R^{18}$ and $R^{19}$ optionally form together with the nitrogen atom they are bonded to, include a 5- to 10-membered aliphatic heterocycle containing carbon atoms and at least one nitrogen atom and, besides these, optionally containing 1 to 3 hetero atoms selected from an oxygen atom, a sulfur atom and a nitrogen atom, such as pyrrolidine, piperidine, morpholine, thiomorpholine, piperazine and the like.

The aliphatic heterocycle is optionally condensed with an aromatic hydrocarbon, and as such an aromatic hydrocarbon, benzene, naphthalene, biphenyl, binaphthyl and the like can be mentioned.

The aliphatic heterocycle optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "homocyclic ring" of the "homocyclic ring optionally having substituent(s)", which $R^4$ and $R^5$ optionally form together with the asymmetric carbons they are respectively bonded to, for example, a cycloalkane having 3 to 7 carbon atoms (e.g., cyclopropane, cyclobutane, cyclopentane, cyclohexane, cycloheptane etc.), a cycloalkene having 4 to 7 carbon atoms (e.g., cyclobutene, cyclopentene, cyclohexene, cycloheptene etc.) and the like, each containing the asymmetric carbons of C* and C** in optically active compound (I), can be mentioned. Preferred are cyclopropane, cyclobutane, cyclopentane, cyclohexane and the like, and more preferred are cyclohexane and the like.

As the "heterocycle" of the "heterocycle optionally having substituent(s)" which $R^4$ and $R^5$ optionally form together with the asymmetric carbons they are respectively bonded to, for example, a 5- to 10-membered heterocycle containing the asymmetric carbons of C* and C** in optically active compound (I), and containing, besides carbon atoms, 1 to 3 hetero atoms selected from an oxygen atom, a sulfur atom and a nitrogen atom (e.g., tetrahydropyran, tetrahydrofuran, pyrrolidine, piperidine and the like) can be mentioned.

The "homocyclic ring" and "heterocycle" are optionally further condensed with an aromatic hydrocarbon (e.g., benzene, naphthalene, biphenyl, binaphthyl etc.).

The "homocyclic ring" and "heterocycle" optionally have substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "protecting group" represented by PG, any protecting group known per se, which is usable as an amino-protecting group, can be used without any particular limitation. To stabilize azo group of azo compound (II), an electron withdrawing protecting group is preferable. As such protecting group, for example, —CO$_2$R$^{11}$, —CONR$^{12}$R$^{13}$ (each symbol is as defined above) and the like can be mentioned, with preference given to an ethoxycarbonyl group, an isopropoxycarbonyl group, a benzyloxycarbonyl group and a tert-butoxycarbonyl group.

The "electron withdrawing group" represented by $R^9$ or $R^{10}$ is not particularly limited as long as the adjacent carbon atom can be acidified to the extent that permits anionation by a basic moiety (amino group) of optically active compound (I). As such electron withdrawing group, for example, a cyano group, a nitro group, —P(=O)R$^{14}$R$^{15}$, —SO$_2$R$^{16}$, —CO$_2$R$^{17}$, —CONR$^{18}$R$^{19}$, —COR$^{20}$ (each symbol is as defined above) and the like can be mentioned, and a cyano group, —CO$_2$R$^{17}$, —COR$^{20}$, —CONR$^{18}$R$^{19}$ and the like are preferable.

The "ring containing an electron withdrawing group" optionally formed by $R^8$ and $R^9$, together with the adjacent carbon atom, may be any as long as the electron withdrawing group has the above-mentioned properties and, for example, a cycloalkanone having 3 to 7 carbon atoms (e.g., cyclopentanone, cyclohexanone, cycloheptanone etc.), a lactone having 3 to 5 carbon atoms (e.g., γ-butyrolactone, δ-valerolactone etc.), a lactam having 3 to 5 carbon atoms (e.g., γ-butyrolactam, δ-valerolactam etc.) and the like, which contain carbonyl as an electron withdrawing group, can be mentioned, with preference given to cyclopentanone, cyclohexanone and the like.

The "ring containing an electron withdrawing group" is optionally further condensed with an aromatic hydrocarbon (e.g., benzene, naphthalene, biphenyl, binaphthyl etc.). As the embodiment of the ring condensed with aromatic hydrocarbon, 1-indanone, 1,2,3,4-tetrahydro-1-oxonaphthalene and the like are preferable.

The "ring containing an electron withdrawing group" optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

The "asymmetric carbon" of C*, C or C* each has an independent absolute configuration, and is not particularly limited. The absolute configurations of C* and C in optically active compound (I) can be appropriately selected to obtain optically active hydrazine compound (IV) having a desired configuration. In optically active hydrazine compound (IV), C* needs to be an asymmetric carbon. Therefore, a compound wherein $R^9$ and $R^{10}$ are simultaneously the same groups is excluded.

Being "optically active" means that it is not an equivalent mixture (e.g., racemate) of isomers having different configuration at the asymmetric carbon. When one of the stereoisomers is present in excess (e.g., a 6:4 mixture), the compound is defined to be optically active.

The compound (III) does not need to be optically active and may be a racemate.

The optically active compound (I), optically active hydrazine compound (IV) and optically active amine compound (V) may be in the form of a salt. As such salt, for example, inorganic acid salts (e.g., hydrochloride, sulfate, nitrate, phosphate etc.); organic acid salts (e.g., acetate, propionate, methanesulfonate, 4-toluenesulfonate, oxalate, maleate etc.); alkali metal salts (e.g., sodium salt, potassium salt etc.); alkaline earth metal salts (e.g., calcium salt, magnesium salt etc.); organic base salts (e.g., trimethylamine salt, triethylamine salt, pyridine salt, picoline salt, dicyclohexylamine salt etc.) and the like can be mentioned.

X in optically active compound (I) is preferably S.

$R^4$ and $R^5$ in optically active compound (I) preferably form, together with the asymmetric carbons they are respectively bonded to, a homocyclic ring optionally having substituent(s) or a heterocycle optionally having substituent(s); they more preferably form, together with the asymmetric carbons they are respectively bonded to, a homocyclic ring optionally having substituent(s); they more preferably form, together with the asymmetric carbons they are respectively bonded to, cyclopropane, cyclobutane, cyclopentane or cyclohexane; and they still more preferably form cyclohexane together with the asymmetric carbons they are respectively bonded to.

When $R^4$ and $R^5$ form cyclohexane together with the asymmetric carbons they are respectively bonded to, $R^6$ and $R^7$ are each preferably a hydrogen atom, and more preferably, the absolute configurations of C* and C** are both S-configurations or both R-configurations.

$R^1$ and $R^2$ in optically active compound (I) are preferably a lower alkyl group optionally having substituent(s), or form, together with the nitrogen atom they are bonded to, an aliphatic heterocycle optionally having substituent(s) and optionally condensed with an aromatic hydrocarbon, more preferably methyl, ethyl or isopropyl, or form isoindoline together with the nitrogen atom they are bonded to, still more preferably methyl or isopropyl.

$R^3$ in optically active compound (I) is preferably an aryl group optionally having substituent(s), more preferably a phenyl group optionally having substituent(s), more preferably a phenyl group substituted by haloalkyl group(s), nitro group(s), cyano group(s) or —$COOR^{21}$ wherein $R^{21}$ is as defined above, more preferably a phenyl group substituted by haloalkyl group(s), still more preferably a phenyl group substituted by trifluoromethyl.

PG of azo compound (II) is preferably an ethoxycarbonyl group, an isopropoxycarbonyl group or a benzyloxycarbonyl group.

2. Production Method of Optically Active Hydrazine Compound (IV) and Optically Active Amine Compound (V)

The production method of the present invention is shown by the following reaction scheme:

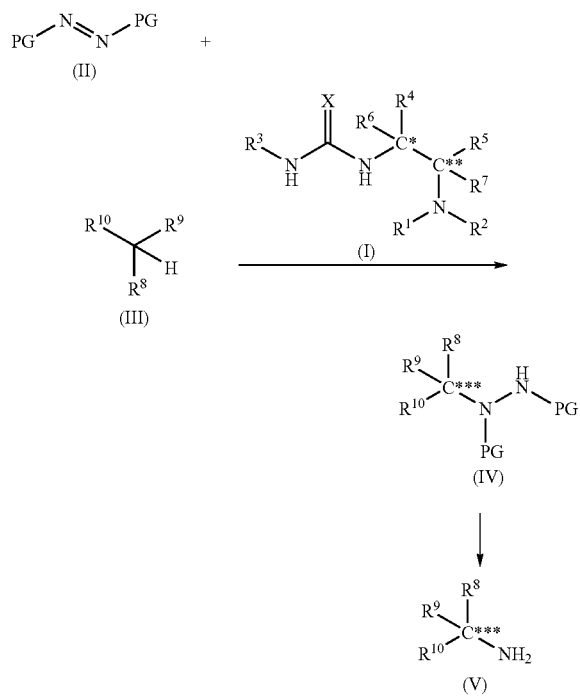

wherein each symbol is as defined above.

In other words, the production method of the present invention includes a method comprising nucleophilic addition of compound (III) to azo compound (II) in the presence of optically active compound (I) to produce optically active hydrazine compound (IV), and a method comprising reacting the optically active hydrazine compound (IV) with a base or an acid to eliminate the protecting group represented by PG, and then subjecting the resulting compound to catalytic-reduction or reacting the resulting compound with a zinc powder to reduce a nitrogen-nitrogen bond, thereby producing optically active amine compound (V).

The optical purity of the optically active hydrazine compound (IV) and optically active amine compound (V) produced according to the production method of the present invention is not particularly limited. The enantiomer excess measured by HPLC chiral analysis is generally not less than 63% e.e., preferably not less than 76% e.e.

The optically active hydrazine compound (IV) can be produced, for example, by mixing optically active compound (I), azo compound (II) and compound (III) in a solvent or without solvent. The order of addition of the reagents is not particularly limited, and optically active compound (I), azo compound (II) and compound (III) can be added simultaneously or successively.

The amount of optically active compound (I) to be used in the production method of the present invention can be a catalytic amount and it is, for example, preferably 0.01 mol to 1 mol, more preferably 0.05 mol to 0.2 mol, per 1 mol of azo compound (II). When the amount of optically active compound (I) to be used is less than this range, the reaction tends to be slow and when it exceeds this range, the effect tends to be less than comparable to its amount of use, which is economically disadvantageous.

The amount of compound (III) to be used in the production method of the present invention is preferably 1 mol to 2 mol, more preferably 1 mol to 1.1 mol, per 1 mol of azo compound (II). When the amount of compound (III) to be used is less than this range, the reaction tends to be incomplete, and when it exceeds this range, the effect tends to be less than comparable to its amount of use, which is economically disadvantageous.

The production method of the present invention can be performed in a solvent or without a solvent. The production method performed without a solvent is economically advantageous because the solvent is not necessary, and is industrially advantageous because the volume efficiency can be increased.

When a solvent is used for the production method of the present invention, the solvent may be any as long as it does not inhibit the reaction and, for example, halogen solvents such as methylene chloride, chloroform, chlorobenzene, α,α,α-trifluorotoluene and the like; diethyl ether, methyl-tert-butyl ether, 1,2-dimethoxyethane, tetrahydrofuran, 1,4-dioxane, ethyl acetate, isopropyl acetate, tert-butyl acetate, hexane, toluene, xylene, acetonitrile and the like can be used alone or in a mixture. In view of superior yield and stereoselectivity, toluene, methylene chloride, diethyl ether or hexane is preferably used, and toluene is particularly preferable.

When a mixed solvent is used, they may be mixed at any ratio.

The amount of the solvent to be used is generally 1 L to 100 L, more preferably 10 L to 50 L, per 1 kg of azo compound (II).

The reaction temperature in the production method of the present invention is generally −78° C. to 100° C., preferably −78° C. to 0° C.

While the reaction time varies depending on the reagent to be used and reaction temperature, it is generally 0.2 hr to 200 hr, preferably 0.25 hr to 100 hr.

The optically active hydrazine compound (IV) produced according to the production method of the present invention can be isolated and purified according to a conventional method. For example, optically active hydrazine compound (IV) can be isolated by pouring a reaction mixture into water to partition the mixture, and washing and concentrating the organic layer under reduced pressure; or by concentrating the reaction mixture. After isolation, the obtained product is purified, for example, by, but not limited to, silica gel column chromatography.

The optically active compound (I) can be easily separated and recovered during isolation and purification of optically active hydrazine compound (IV). For example, since basic amine is present in optically active compound (I), compound (I) can be separated from optically active hydrazine compound (IV) during extraction by transferring compound (I) in the form of a salt into the aqueous layer by treating the mixture with an aqueous acidic solution (e.g., hydrochloric acid, nitric acid, sulfuric acid etc.). After neutralization of the aqueous solution, it is extracted with an organic solvent (e.g., ethyl acetate, toluene, chloroform, methylene chloride etc.) to recover optically active compound (I). It may also be separated and recovered by silica gel column chromatography.

The optically active compound (I) separated and recovered in this manner can be re-used for the production method of the present invention. That is, since optically active compound (I) of the present invention is non-metal, degradation of catalytic activity as observed in metal catalysts etc. does not occur easily, and compound (I) can be re-used as many times as desired upon recovery, which is economically advantageous.

The optically active hydrazine compound (IV) obtained in the above can be led to optically active amine compound (V) by a reaction according to a method known per se, such as the method described in 1) Angew. Chem. Int. Ed. 2002, 41, 1790-1793 or 2) J. Am. Chem. Soc. 2004, 126, 8120-8121.

To be specific, optically active amine compound (V) can be produced, for example, by reacting optically active hydrazine compound (IV) with a base or an acid in a solvent or without solvent to eliminate the protecting group represented by PG, and then subjecting the resulting compound to catalytic reduction or reacting the resulting compound with a zinc powder to reduce a nitrogen-nitrogen bond. The detail of the reaction conditions is omitted because the reactions can be carried out according to the above-mentioned references.

The optically active hydrazine compound (IV) and optically active amine compound (V) produced according to the production method of the present invention can be useful synthesis intermediates for amines, amino acids, pharmaceutical agents, agricultural chemicals, food additives and the like.

The optically active compound (I) to be used in the present invention can be produced by the method described in WO2005/000803.

The azo compound (II), which is a starting material of the production method of the present invention, can be a commercially available product.

The compound (III), which is a starting material of the present invention, can be selected without limitation from known compounds according to the object.

EXAMPLES

The present invention is explained more specifically in the following by referring to Examples, which are not to be construed as limitative.

Preparation Example 1

(R,R)-trans-1-[3,5-bis(trifluoromethyl)phenyl]-3-[2-(N,N-dimethylamino)cyclohexyl]thiourea

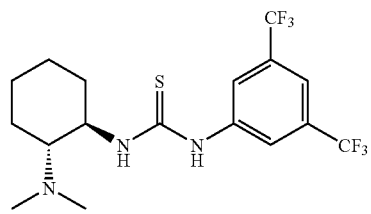

To a solution of 3,5-bis(trifluoromethyl)phenyl isothiocyanate (605 mg, 2.23 mmol) in dry tetrahydrofuran (1.0 mL) was added (R,R)-trans-N,N-dimethyl-1,2-diaminocyclohexane (317 mg, 2.23 mmol) under an argon atmosphere. The reaction mixture was stirred at room temperature for 3 hr, and concentrated under reduced pressure. The obtained residue was purified by silica gel column chromatography (elution solvent: chloroform/methanol/triethylamine=100/5/1) to give the title compound as a white amorphous solid (597 mg, yield 65%).

$[\alpha]_D^{16}$=−32.7 (c 0.99, CHCl$_3$);
$^1$H-NMR (500 MHz, DMSO-d$_6$) δ: 10.0 (S, 1H), 8.21 (s, 1H), 8.17 (s, 2H), 7.66 (s, 1H), 4.09 (brs, 1H), 2.54 (brs, 1H), 2.21 (s, 7H), 1.82 (brs, 1H), 1.74 (brs, 1H), 1.63 (brd, J=11.0 Hz, 1H), 1.31-1.01 (m, 4H) ppm;
$^{13}$C-NMR (126 MHz, DMSO-d$_6$) δ: 178.6, 142.0, 130.8, 130.5, 130.3, 130.0, 126.5, 124.3, 122.2, 120.9, 120.0, 115.3, 65.0, 55.3, 45.7, 31.6, 24.6, 24.5, 21.0 ppm;
IR (CHCl$_3$) ν: 3402, 3200, 2942, 2865, 1528, 1469, 1383, 1278 cm$^{-1}$;
MS (FAB$^+$) 414 (MH$^+$, 100);
Elemental Analysis
Calcd (for C$_{17}$H$_{21}$F$_6$N$_3$S): C, 49.39; H, 5.12; N, 10.16; F, 27.57.
Found: C, 49.36; H, 5.28; N, 10.11; F, 27.71.

Example 1 ethyl(S)-N,N'-bis(isopropoxycarbonyl)-2-cyano-2-hydrazino-2-phenylacetate

To a solution of ethyl 2-cyano-2-phenylacetate (23.0 mg, 0.11 mmol) and (R,R)-trans-1-[3,5-bis(trifluoromethyl)phenyl]-3-[2-(N,N-dimethylamino)cyclohexyl]thiourea (4.1 mg, 0.01 mmol) in toluene (1 mL) was added diisopropyl azodicarboxylate (21.5 μL, 0.10 mmol) at −78° C. After stirring for 15 min, the reaction mixture was concentrated. The residue was purified by silica gel column (hexane/ethyl acetate=3/1) to give the title compound (41.4 mg, yield: 100%, optical purity: 76% ee). Colorless amorphous
$^1$H-NMR (500 MHz, CDCl$_3$) δ: 0.99 and 1.16 (each d, J=6.1 Hz, total 3H), 1.20-1.40 (m, 6H), 4.20-4.40 (m, 2H), 4.75-4.95 (m, 1H), 5.08 (m, 1H), 6.11 and 6.29 (each brs, total 1H), 7.35-7.50 (m, 3H), 7.60-7.85 (m, 2H) ppm;
IR (CHCl$_3$) ν 3412, 2986, 1753, 1739, 1726 cm$^{-1}$;
MS (FAB$^+$) 392 (MH$^+$, 97), 237 (100);
HRMS (FAB$^+$) Calcd for [C$_{19}$H$_{25}$N$_3$O$_6$]$^+$: 392.1822.
Found: 392.1823.
HPLC analysis conditions: Chiralcel AD, hexane/2-propanol=90/10, 0.5 mL/min, λ=210 nm, retention time: (major) 55.9 min, (minor) 37.1 min.

Example 2

N,N'-bis(isopropoxycarbonyl)-2-acetyl-2-hydrazinocyclopentanone

To a solution of 2-acetyl-cyclopentanone (13.9 mg, 0.11 mol) and (R,R)-trans-1-[3,5-bis(trifluoromethyl)phenyl]-3-[2-(N,N-dimethylamino)cyclohexyl]thiourea (4.1 mg, 0.01 mmol) in toluene (1 mL) was added diisopropyl azodicarboxylate (21.5 µL, 0.10 mmol) at −78° C. After stirring for 18 hr, the reaction mixture was concentrated. The residue was purified by silica gel column (hexane/ethyl acetate=3/1) to give the title compound (31.8 mg, yield: 97%, optical purity: 77% ee). Colorless oil $[\alpha]_D^{26}$=+33.4 (c 1.22, $CHCl_3$);

$^1$H-NMR (500 MHz, $CDCl_3$) δ: 1.20-1.40 (m, 12H), 1.65-2.85 (m, 9H), 4.94 (brs, 2H), 6.60 (brs, 1H) ppm;

IR ($CHCl_3$) ν 3018, 1759, 1746, 1733, 1720 $cm^{-1}$;

MS ($FAB^+$) 329($MH^+$, 100);

HRMS ($FAB^+$) Calcd for $[C_{16}H_{24}N_2O_6]^+$: 329.1713. Found: 329.1707.

HPLC conditions: Chiralcel AD, hexane/2-propanol=90/10, 0.5 mL/min, λ=210 nm, retention time (major) 24.6 min, (minor) 18.0 min

Example 3 methyl N,N'-bis(ethoxycarbonyl)-1-hydrazino-2-oxocyclopentanecarboxylate

To a solution of methyl 2-oxocyclopentanecarboxylate (15.6 mg, 0.11 mmol) and (R,R)-trans-1-[3,5-bis(trifluoromethyl)phenyl]-3-[2-(N,N-dimethylamino)cyclohexyl]thiourea (4.1 mg, 0.01 mmol) in toluene (1 mL) was added diethyl azodicarboxylate (45.5 µL, 0.10 mmol) at room temperature. After stirring for 0.5 hr, the reaction mixture was concentrated. The residue was purified by silica gel column (hexane/ethyl acetate=3/1) to give the title compound (41.4 mg, yield: 92%).

The enanthioselectivity was 80% ee by chiral HPLC analysis (Chiralpak AD column, hexane/2-propanol=90/10, 1.0 mL/min, λ=254 nm, retention time (major)=11.7 min, (minor)=9.8 min).

$[\alpha]_D^{25}$=+18.00 (c 1.00, $CHCl_3$);

IR ($CHCl_3$) ν 3398, 3027, 2360, 1738, 1215 $cm^{-1}$;

$^1$H-NMR (500 MHz, $CDCl_3$) δ: 6.96 (brs, 1H), 4.10-4.20 (m, 4H), 3.78 (s, 3H), 2.60-2.10 (m, 6H), 1.25-1.32 (m, 6H) ppm;

$^{13}$C-NMR (126 MHz, $CDCl_3$) δ: 171.0, 156.0, 155.4, 63.0, 62.1, 60.1, 53.0, 22.4, 20.7, 18.4, 14.1 ppm;

MS ($FAB^-$) 317($MH^+$, 100), 185(75);

HRMS ($FAB^+$) Calcd for $[C_{13}H_{21}N_2O_7]^+$: 317.1349. Found: 317.1343.

Example 4 methyl N,N'-bis(isopropoxycarbonyl)-2-hydrazino-[1,2,3,4-tetrahydro-1-oxonaphthalene]-2-carboxylate To a solution of methyl 1,2,3,4-tetrahydro-1-oxonaphthalene-2-carboxylate (22.5 mg, 0.11 mmol) and (R,R)-trans-1-[3,5-bis(trifluoromethyl)phenyl]-3-[2-(N,N-dimethylamino)cyclohexyl]thiourea (4.1 mg, 0.01 mmol) in toluene (1 mL) was added diisopropyl azodicarboxylate (21.5 µL, 0.10 mmol) at −78° C. After stirring for 168 hr, the reaction mixture was concentrated. The residue was purified by silica gel column (hexane/ethyl acetate=3/1) to give the title compound (38.6 mg, yield: 95%, optical purity: 79% ee). Colorless oil $[\alpha]_D^{25}$=+5.60 (c 1.14, $CHCl_3$);

IR ($CHCl_3$) ν 3366, 3039, 2985, 2947, 1746, 1732, 1706 $cm^{-1}$;

$^1$H-NMR (500 MHz, $CDCl_3$) δ: 1.00-1.48 (m, 12H), 2.52-3.54 (m, 4H), 3.81 (s, 3H), 4.71 and 4.98 (each s, total 2H), 6.41 (s, 1H), 7.25-7.45 (m, 2H), 7.45-7.51 (m, 1H), 7.85-8.05 (m, 1H) ppm;

MS ($FAB^+$) 407($MH^+$, 100), 205(100);

HRMS ($FAB^+$) Calcd for $[C_{20}H_{27}N_2O_7]^+$: 407.1818. Found: 407.1826.

HPLC conditions: Chiralcel OD-H, hexane/2-propanol=90/10, 0.5 mL/min, λ=254 nm, retention time (major) 14.3 min, (minor) 18.4 min This application is based on patent application No. 2005-54799 filed in Japan, the contents of which are hereby incorporated by reference.

What is claimed is:

1. A production method of a compound represented by the formula (IV):

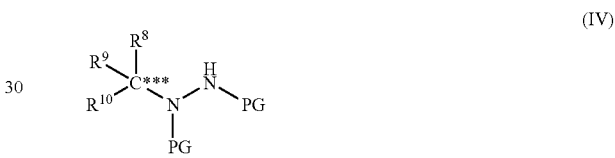

(IV)

wherein $R^8$ is a hydrogen atom, a lower alkyl group optionally having substituent(s), an aralkyl group optionally having substituent(s), an aryl group optionally having substituent(s) or a heteroaryl group optionally having substituent(s);

$R^9$ and $R^{10}$ are each independently an electron withdrawing group, or $R^8$ and $R^9$ optionally form, together with the adjacent carbon atom, a ring containing an electron withdrawing group and optionally having substituent(s) (said ring is optionally condensed with an aromatic hydrocarbon), provided that $R^9$ and $R^{10}$ are not the same group;

C*** is an asymmetric carbon; and

PG is a protecting group, or a salt thereof, which comprises reacting a compound represented by the formula (II):

(II)

wherein PG is as defined above, with a compound represented by the formula (III):

(III)

wherein $R^8$, $R^9$ and $R^{10}$ are as defined above, in the presence of a compound represented by the formula (I):

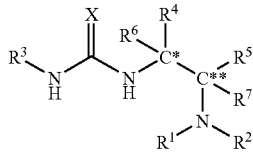

wherein

X is S or O;

C* and C** are each independently an asymmetric carbon;

$R^1$ and $R^2$ are the same or different and each is a lower alkyl group optionally having substituent(s), an aralkyl group optionally having substituent(s) or an aryl group optionally having substituent(s), or $R^1$ and $R^2$ optionally form, together with the nitrogen atom they are bonded to, an aliphatic heterocycle optionally having substituent(s) (the aliphatic heterocycle is optionally condensed with an aromatic hydrocarbon);

$R^3$ is a lower alkyl group optionally having substituent(s), an aralkyl group optionally having substituent(s), an aryl group optionally having substituent(s) or a heteroaryl group optionally having substituent(s);

$R^4$ and $R^5$ are the same or different and each is a lower alkyl group optionally having substituent(s), an aralkyl group optionally having substituent(s) or an aryl group optionally having substituent(s), or $R^4$ and $R^5$ optionally form, together with the asymmetric carbons they are respectively bonded to, a homocyclic ring optionally having substituent(s) or a heterocycle optionally having substituent(s) (the homocyclic ring and the heterocycle are each optionally condensed with an aromatic hydrocarbon); and $R^6$ and $R^7$ are the same or different and each is a hydrogen atom or a lower alkyl group optionally having substituent(s), or a salt thereof.

2. The method of claim 1, wherein X is S.

3. The method of claim 1, wherein $R^4$ and $R^5$ form, together with the asymmetric carbons they are respectively bonded to, cyclopropane, cyclobutane, cyclopentane or cyclohexane.

4. The method of claim 3, wherein $R^4$ and $R^5$ form cyclohexane together with the asymmetric carbons they are respectively bonded to, and $R^6$ and $R^7$ are each a hydrogen atom.

5. The method of claim 4, wherein the absolute configurations of C* and C** are both S-configurations or both R-configurations.

6. The method of claim 1, wherein the protecting group is —CO$_2$R$^{11}$ or —CONR$^{12}$R$^{13}$ wherein $R^{11}$, $R^{12}$ and $R^{13}$ are each independently a lower alkyl group optionally having substituent(s), an aralkyl group optionally having substituent(s), an aryl group optionally having substituent(s) or a heteroaryl group optionally having substituent(s), or $R^{12}$ and $R^{13}$ optionally form, together with the nitrogen atom they are bonded to, an aliphatic heterocycle optionally having substituent(s) (the aliphatic heterocycle is optionally condensed with an aromatic hydrocarbon).

7. The method of claim 1, wherein the electron withdrawing group is a cyano group, a nitro group, —P(=O)R$^{14}$R$^{15}$, —SO$_2$R$^{16}$, —CO$_2$R$^{17}$, —CONR$^{18}$R$^{19}$ or —COR$^{20}$ wherein $R^{14}$, $R^{15}$, $R^{16}$, $R^{17}$, $R^{18}$, $R^{19}$ and $R^{20}$ are each independently a hydrogen atom, a lower alkyl group optionally having substituent(s), an aralkyl group optionally having substituent(s), an aryl group optionally having substituent(s) or a heteroaryl group optionally having substituent(s), or $R^{18}$ and $R^{19}$ optionally form, together with the nitrogen atom they are bonded to, an aliphatic heterocycle optionally having substituent(s) (the aliphatic heterocycle is optionally condensed with an aromatic hydrocarbon).

8. The method of claim 1, wherein the ring containing an electron withdrawing group, which is optionally formed by $R^8$ and $R^9$ is cyclopentanone, cyclohexanone, 1-indanone or 1,2,3,4-tetrahydro-1-oxonaphthalene.

9. The method of claim 1, wherein the reaction is performed in at least one solvent selected from toluene, methylene chloride, diethyl ether and hexane.

10. A production method of a compound represented by the formula (V):

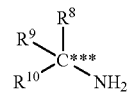

wherein $R^8$ is a hydrogen atom, a lower alkyl group optionally having substituent(s), an aralkyl group optionally having substituent(s), an aryl group optionally having substituent(s) or a heteroaryl group optionally having substituent(s);

$R^9$ and $R^{10}$ are each independently an electron withdrawing group, or $R^8$ and $R^9$ optionally form, together with the adjacent carbon atom, a ring containing an electron withdrawing group and optionally having substituent(s) (said ring is optionally condensed with an aromatic hydrocarbon), provided that $R^9$ and $R^{10}$ are not the same group; and C*** is an asymmetric carbon;

or a salt thereof, which comprises reacting a compound represented by the formula (II):

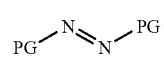

wherein PG is a protecting group, with a compound represented by the formula (III):

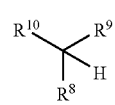

wherein $R^8$, $R^9$ and $R^{10}$ are as defined above, in the presence of a compound represented by the formula (I):

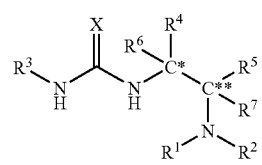

wherein
X is S or O;
C* and C** are each independently an asymmetric carbon;
$R^1$ and $R^2$ are the same or different and each is a lower alkyl group optionally having substituent(s), an aralkyl group optionally having substituent(s) or an aryl group optionally having substituent(s), or $R^1$ and $R^2$ optionally form, together with the nitrogen atom they are bonded to, an aliphatic heterocycle optionally having substituent(s) (the aliphatic heterocycle is optionally condensed with an aromatic hydrocarbon);
$R^3$ is a lower alkyl group optionally having substituent(s), an aralkyl group optionally having substituent(s), an aryl group optionally having substituent(s) or a heteroaryl group optionally having substituent(s);
$R^4$ and $R^5$ are the same or different and each is a lower alkyl group optionally having substituent(s), an aralkyl group optionally having substituent(s) or an aryl group optionally having substituent(s), or $R^4$ and $R^5$ optionally form, together with the asymmetric carbons they are respectively bonded to, a homocyclic ring optionally having substituent(s) or a heterocycle optionally having substituent(s) (the homocyclic ring and the heterocycle are each optionally condensed with an aromatic hydrocarbon); and $R^6$ and $R^7$ are the same or different and each is a hydrogen atom or a lower alkyl group optionally having substituent(s), or a salt thereof, to give optically active hydrazine compound (IV):

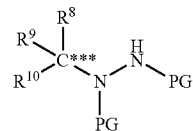

(IV)

wherein each symbol is as defined above, or a salt thereof, reacting the optically active hydrazine compound (IV) or a salt thereof with a base or an acid to eliminate the protecting group represented by PG, and then subjecting the resulting compound to catalytic reduction or reacting the resulting compound with a zinc powder to reduce a nitrogen-nitrogen bond.

11. The method of claim 10, wherein X is S.

* * * * *

UNITED STATES PATENT AND TRADEMARK OFFICE
CERTIFICATE OF CORRECTION

PATENT NO. : 7,655,817 B2 Page 1 of 1
APPLICATION NO. : 11/341852
DATED : February 2, 2010
INVENTOR(S) : Takemoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 977 days.

Signed and Sealed this

Twenty-third Day of November, 2010

David J. Kappos
*Director of the United States Patent and Trademark Office*